United States Patent [19]

Mattes et al.

[11] 4,341,852

[45] Jul. 27, 1982

[54] POLYCYANOANTHRACENES AND USE AS SENSITIZERS FOR ELECTROPHOTOGRAPHIC COMPOSITIONS

[75] Inventors: Susan L. Mattes; Samir Y. Farid, both of Rochester, N.Y.

[73] Assignee: Eastman Kodak Company, Rochester, N.Y.

[21] Appl. No.: 193,062

[22] Filed: Oct. 2, 1980

[51] Int. Cl.$^3$ .......................... G03G 5/09; G03G 5/06; C07C 121/64

[52] U.S. Cl. .......................................... 430/83; 430/81; 430/900; 260/465 H

[58] Field of Search ...................... 430/72, 81, 83, 900; 260/465 H

[56] References Cited

U.S. PATENT DOCUMENTS 3,297,739 1/1967 Wallenfels et al. ............ 260/465 H 3,549,361 12/1970 Miller .................................. 430/72

FOREIGN PATENT DOCUMENTS 1021994 3/1966 United Kingdom ................. 430/72

OTHER PUBLICATIONS

"Photoconductors Containing Cyano-Substituted Polynuclear Compounds", Res. Discl. No. 102, Oct. 1972, pp. 40-41.

Mattes et al., "Photosensitized Electron-Transfer Reactions of Phenylacetylene", J.C.S. Chem. Comm., 1980 pp. 126-128.

*Primary Examiner*—Roland E. Martin, Jr.

*Attorney, Agent, or Firm*—Joshua G. Levitt

[57] ABSTRACT

Polycyanoanthracenes containing three or more cyano groups, and in particular the novel compound 2,6,9,10-tetracyanoanthracene, are sensitizers for organic photoconductors.

5 Claims, No Drawings

POLYCYANOANTHRACENES AND USE AS SENSITIZERS FOR ELECTROPHOTOGRAPHIC COMPOSITIONS

This invention relates to organic compounds useful as sensitizers in photoconductive compositions and electrophotographic elements. Certain of these sensitizers are novel compounds.

The process of xerography, as disclosed by Carlson in U.S. Pat. No. 2,297,691, employs an electrophotographic element comprising a support material bearing a coating of a normally insulating material the electrical resistance of which varies with the amount of incident actinic radiation it receives during an imagewise exposure. The element is then exposed to a pattern of actinic radiation which has the effect of differentially reducing the potential of the surface charge in accordance with the relative energy contained in various parts of the radiation pattern. The differential surface charge, or electrostatic latent image, remaining on the electrophotographic element is then made visible by contacting the surface with a suitable electroscopic marking material. Such marking material, or toner, whether contained in an insulating liquid or on a dry carrier, can be deposited on the exposed surface in accordance with either the charge pattern or the absence of charge pattern as desired. The deposited marking material can then be either permanently fixed to the surface of the sensitive element by known means such as heat, pressure, solvent vapor and the like or transferred to a second element to which it is similarly fixed. Likewise, the electrostatic latent image can be transferred to a second element and developed there.

Various photoconductive insulating materials have been employed in the manufacture of electrophotographic elements. For example, vapors of selenium and vapors of selenium alloys deposited on a suitable support and particles of photoconductive zinc oxide held in a resinous, film-forming binder have found wide application in present-day document copying applications.

Since the introduction of electrophotography, a great many organic compounds have been found to possess some degree of photoconductivity. Many organic compounds such as trinitrofluorenone have revealed a useful level of photoconduction and have been incorporated into photoconductive compositions. Optically clear organic photoconductor-containing elements having desirable electrophotographic properties are especially useful in electrophotography. Such electrophotographic elements may be exposed through a transparent base, if desired, thereby providing unusual flexibility in equipment design. Such compositions when coated as a film or layer on a suitable support also yield an element which is reusable; that is, it can be used to form subsequent images after residual toner from prior images has been removed by transfer and/or cleaning.

Although many of the organic photoconductor materials are inherently light sensitive, their degree of sensitivity is usually low so that it is often necessary to add materials to increase their speed. Increasing the electrophotographic speed has several advantages in that it reduces exposure time, allows projection printing through various optical systems, etc. By increasing speed through the use of sensitizers, photoconductors which would otherwise have been unsatisfactory are useful in processes where higher speeds are required. Accordingly, there is a need for new materials useful as sensitizers of organic photoconductor-containing systems.

In accordance with the present invention, it has been discovered that organic photoconductive compositions containing a sensitizing amount of a polycyanoanthracene containing three or more cyano groups exhibit good electrophotographic speed in the visible spectrum, especially in the blue region of the visible spectrum. Sensitizers useful in the present invention include tri- and tetracyanoanthracenes. Especially useful is the novel compound 2,6,9,10-tetracyanoanthracene, which has the structure:

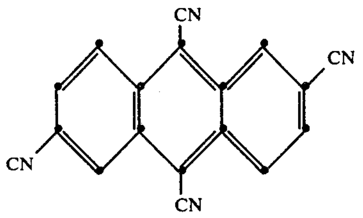

These polycyanoanthracenes are electron acceptors and therefore are particularly effective as sensitizers for organic photoconductors which are electron donors.

The known polycyanoanthracenes employed in this invention can be prepared by procedures known in the art. The novel 2,6,9,10-tetracyanoanthracene can be prepared by bromination of anthracene followed by a displacement reaction with cuprous cyanide in the presence of N,N-dimethylacetamide to form the desired nitrile. Depending on the amount of bromide and reaction time 2,9,10-tribromoanthracene can be prepared and converted to the corresponding trinitrile if desired. However, continued bromination produces the preferred tetra-substituted compound.

Electrophotographic elements can be prepared with a variety of photoconductive compounds and the sensitizing compounds of this invention in the usual manner, i.e., by blending a dispersion or solution of the photoconductive compound together with an electrically insulating, film-forming resin binder, when necessary or desirable, and coating or forming a self-supporting layer with the photoconductive composition. Generally, a suitable amount of the sensitizing compound is mixed with the photoconductive coating composition so that after thorough mixing, the sensitizing compound is uniformly distributed throughout the desired layer of the coated element. The amount of sensitizer that can be added to a photoconductor-containing layer to give effective increases in speed can vary widely. The optimum concentration in any given case will vary with the specific photoconductor and sensitizing compound used.

In general, the sensitizer is added in a concentration range from about 0.0001 to about 30 percent by weight based on the weight of the film-forming coating composition. Normally, the sensitizer is added to the coating composition in an amount from about 0.005 to about 10 percent by weight of the total coating composition.

The sensitizers used in this invention are effective for enhancing the electrophotosensitivity of a wide variety of photoconductors. Photoconductors useful in sensitive compositions containing the present sensitizers include:

1. Arylamine photoconductors including substituted and unsubstituted arylamines, diarylamines, nonpolymeric triarylamines and polymeric triarylamines such as those described in Fox U.S. Pat. No. 3,240,597, issued Mar. 15, 1966 and Klupfel et al U.S. Pat. No. 3,180,730, issued Apr. 27, 1965;

2. Polyarylalkane photoconductors of the types described in Noe et al U.S. Pat. No. 3,274,000, issued Sept. 20, 1966, Wilson U.S. Pat. No. 3,542,547, issued Nov. 24, 1970, and in Seus et al U.S. Pat. No. 3,542,544, issued Nov. 24, 1970;

3. 4-Diarylamino-substituted chalcones of the types described in Fox U.S. Pat. No. 3,526,501, issued Sept. 1, 1970;

4. Non-ionic cycloheptyl compounds of the types described in Looker U.S. Pat. No. 3,533,786, issued Oct. 13, 1970;

5. Compounds containing an

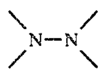

nucleus, as described in Fox U.S. Pat. No. 3,542,546, issued Nov. 24, 1970;

6. Organic compounds having a 3,3'-bis-aryl-2-pyrazoline nucleus, as described in Fox et al U.S. Pat. No. 3,527,602, issued Sept. 8, 1970;

7. Triarylamines in which at least one of the aryl radicals is substituted by either a vinyl radical or a vinylene radical having at least one active hydrogen-containing group, as described in Brantly et al U.S. Pat. No. 3,567,450, issued Mar. 2, 1971;

8. Triarylamines in which at least one of the aryl radicals is substituted by an active hydrogen-containing group, as described in Brantly et al Belgian Pat. No. 728,563, dated Apr. 30, 1969;

9. Any other organic compound which exhibits photoconductive properties such as those set forth in Australian Pat. No. 248,402 and the various polymeric photoconductors such as the photoconductive carbazol polymers described in U.S. Pat. No. 3,421,891, dated Jan. 14, 1969.

Preferred binders for use in preparing photoconductive layers sensitized in accordance with this invention comprise polymers having fairly high dielectric strength which are good electrically insulating film-forming vehicles. Materials of this type include styrene-butadiene copolymers; silicone resins; styrene-alkyd resins; silicone alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals), such as poly(vinyl butyral); polyacrylic and methacrylic esters, such as poly(methyl methacrylate), poly(n-butyl methacrylate), poly(isobutyl methacrylate), etc; polystyrene; nitrated polystyrene; polymethylstyrene; isobutylene polymers; polyesters, such as poly(ethylene alkaryloxyalkylene terephthalate); phenol-formaldehyde resins; ketone resins; polyamides; polycarbonates; polythiocarbonates, poly(ethylene-co-2,2-isopropylidenebis(phenyleneoxyethylene) terephthalate); nuclear substituted poly(vinyl haloarylates); etc. Suitable resins of the type contemplated for use in the photoconductive layers of the invention are sold under such trademarks as Vitel PE-101, Cymac, Piccopale 100, Saran F-220, Lexan F-220 and Lexan 105 and 145. Other types of binders which can be used in the photoconductive layers of the invention include such materials as paraffin, mineral waxes, etc. If a polymeric photoconductor is used, the binder may be omitted altogether.

The organic coating solvents useful in preparing the above photoconductive composition can be selected from a variety of materials. Useful liquids are hydrocarbon solvents, including substituted hydrocarbon solvents, with preferred materials being halogenated hydrocarbon solvents. The requisite properties of the solvent are that it be capable of dissolving the sensitizer and capable of dissolving or at least swelling or solubilizing the polymeric ingredient of the composition. In addition, it is helpful if the solvent is volatile, preferably having a boiling point of less than about 200° C. Particularly useful solvents include halogenated lower alkanes having from 1 to about 3 carbon atoms, such as dichloromethane, dichloroethane, dichloropropane, trichloromethane, trichloroethane, tribromomethane, trichloromonofluromethane, trichlorotrifluoroethane, etc.; aromatic hydrocarbons such as benzene, toluene, as well as halogenated benzene compounds such as chlorobenzene, bromobenzene, dichlorobenzene, etc.; ketones such as dialkyl ketones having 1 to about 3 carbon atoms in the alkyl moiety such as dimethyl ketone, methyl ethyl ketone, etc.; and ethers such as tetrahydrofuran, etc. Mixtures of these and other solvents can also be used.

In preparing the photoconductive coating composition, useful results are obtained where the photoconductor is present in an amount equal to at least about 1 weight percent of the coating composition. The upper limit in the amount of photoconductor present can be widely varied in accordance with usual practice. In those cases where a binder is employed, it is normally required that the photoconductor be present in an amount from about 1 weight percent of the coating composition to about 99 weight percent of the coating composition. A polymeric photoconductor can be employed in which case an additional binder may not be required. A preferred weight range for the photoconductor in the coating composition is from about 10 weight percent to about 60 weight percent.

Suitable supporting materials for coating photoconductive layers of this invention can include any of a wide variety of electrically conducting supports, for example, paper (at a relative humidity above 20 percent); aluminum-paper laminates; metal foils such as aluminum foil, zinc foil, etc.; metal plates, such as aluminum, copper, zinc, brass, and galvanized plates; vapor deposited metal layers such as silver, nickel, aluminum and the like coated on paper or conventional photographic film bases such as cellulose acetate, poly(ethylene terephthalate), polystyrene, etc. Such conducting materials as nickel can be vacuum deposited on transparent film supports in sufficiently thin layers to allow electrophotographic elements prepared therewith to be exposed from either side of such elements. An especially useful conducting support can be prepared by coating a support material such as poly(ethylene terephthalate) with a conducting layer containing a semiconductor dispersed in a resin. Such conducting layers both with and without insulating barrier layers are described in U.S. Pat. No. 3,245,833. Likewise, a suitable conducting coating can be prepared from the sodium salt of a carboxyester lactone of maleic anhydride and a vinyl acetate polymer. Such kinds of conducting layers and methods for their optimum preparation and use are disclosed in U.S. Pat. Nos. 3,007,901 and 3,262,807.

Coating thicknesses of the photoconductive composition on the support can vary widely. Normally, a coating in the range of about 10 microns to about 300 microns before drying is useful for the practice of this invention. The preferred range of coating thickness is in the range from about 50 microns to about 150 microns before drying, although useful results can be obtained outside of this range. The resultant dry thickness of the coating is preferably between about 2 microns and about 50 microns, although useful results can be obtained with a dry coating thickness between about 1 and about 200 microns.

The elements of this invention can be employed in any of the well known electrophotographic processes which require photoconductive layers. One such process is the xerographic process. In a process of this type, an electrophotographic element is held in the dark and given a blanket electrostatic charge by placing it under a corona discharge. This uniform charge is retained by the layer because of the substantial dark insulating property of the layer, i.e., the low conductivity of the layer in the dark. The electrostatic charge formed on the surface of the photoconductive layer is then selectively dissipated from the surface of the layer by imagewise exposure to light by means of a conventional exposure operation such as, for example, by a contact-printing technique, or by lens projection of an image, and the like, to thereby form a latent electrostatic charge by virtue of the fact that light energy striking the photoconductor causes the electrostatic charge in the light struck areas to be conducted away from the surface in proportion to the intensity of the illumination in a particular area.

The charge pattern produced by exposure is then developed or transferred to another surface and developed there, i.e., either the charged or uncharged areas rendered visible, by treatment with a medium comprising electrostatically responsive particles having optical density. The developing electrostatically responsive particles can be in the form of a dust, i.e., powder, or a pigment in a resinous carier, i.e., toner. A preferred method of applying such toner to a latent electrostatic image for solid area development is by the use of a magnetic brush. Methods of forming and using a magnetic brush toner applicator are described in the following U.S. Patents: Young U.S. Pat. No. 2,786,439, issued Mar. 26, 1957; Giaimo U.S. Pat. No. 2,786,440, issued Mar. 26, 1957; Young U.S. Pat. No. 2,786,441, issued Mar. 26, 1957; and Greig U.S. Pat. No. 2,874,063, issued Feb. 17, 1959. Liquid development of the latent electrostatic image also may be used. In liquid development, the developing particles are carried to the image-bearing surface in an electrically insulating liquid carrier. Methods of development of this type are widely known and have been described in the patent literature, for example, Metcalfe et al U.S. Pat. No. 2,907,674, issued Oct. 6, 1959. In dry developing processes, the most widely used method of obtaining a permanent record is achieved by selecting a developing particle which has as one of its components a low-melting resin. Heating the powder image then causes the resin to melt or fuse into or on the element. The powder is, therefore, caused to adhere permanently to the surface of the photoconductive layer. In other cases, a transfer of the electrostatic charge image formed on the photoconductive layer can be made to a second support such as paper which would then become the final print after development and fusing. Techniques of the type indicated are well known in the art and have been described in the literature in "RCA Review", Vol. 15 (1954), pages 469–484.

The following examples are included for a further understanding of the invention.

EXAMPLE 1

Preparation of 2,6,9,10-tetracyanoanthracene

Bromine (115 g, 1.72 moles) in 70 mL of nitrobenzene was added dropwise to a hot (100° C.) solution of 101 g (0.30 moles) of 9,10-dibromoanthracene in 700 mL of nitrobenzene under a nitrogen atmosphere. After addition, the mixture was stirred at 130° C. for 3 hours, 150° C. for 3 hours, heated to 200° C. for 10 minutes and allowed to cool at room temperature overnight. The solid product was collected by filtration and digested several times with boiling dichloromethane to give a mixture of 2,9,10-tribromoanthracene (5–10 percent) and 2,6,9,10-tetrabromoanthracene (determined by gas chromatography analysis). This mixture was subjected to a second treatment with bromine (1 equiv., 1 hour at 150° C., 1 hour at 170° C., 10 minutes at 200° C.). The solid product was digested several times with boiling dichloromethane to give 66 g (0.13 moles, 43 percent) of 2,6,9,10-tetrabromoanthracene (100 percent by gas chromotography), m.p. 293°–296° C.

A mixture of 66 g (0.13 mole) of 2,6,9,10-tetrabromoanthracene and 116 g (1.3 mole) of cuprous cyanide in 1.5 L of freshly distilled N,N-dimethylacetamide was refluxed under nitrogen for 4 hours. The reaction mixture was allowed to cool to room temperature and hydrogen sulfide was bubbled through it for 30 minutes. This mixture was stirred at ambient temperature, under nitrogen, overnight. A black solid was collected by filtration and extracted repeatedly with boiling toluene. All the toluene extracts were combined and evaporated to dryness to give the crude product. This solid was digested with acetonitrile to give 18 g (0.065 mole, 50 percent) of 2,6,9,10-tetracyanoanthracene. It was further purified by several recrystallizations from nitromethane; m.p. 345° C. The NMR, infrared, and mass spectral analyses were consistent with the assigned structure and molecular weight.

EXAMPLE 2

An electrically insulating photoconductive composition was prepared by combining 0.70 g Lexan® polycarbonate resin binder, 0.30 g tritolylamine photoconductor, and 13.3 g dichloromethane saturated with 2,6,9,10-tetracyanoanthracene sensitizer (ca. $1.4\times10^{-3}$ mol/L). The composition was coated at 6 mil wet thickness on a 4 mil poly(ethylene terephthalate) support bearing a vapor deposited nickel conductive layer. The resulting film was charged (positively) to ca. 300 V, exposed for 10 sec using a 500 W tungsten lamp and developed with a conventional liquid electrostatic developer comprising positively charged toner particles in Isopar G solvent to give a very good negative image.

The invention has been described in detail with particular reference to preferred embodiments thereof, but it will be understood that variations and modifications can be effected within the spirit and scope of the invention.

We claim:

1. An electrically insulating organic photoconductive composition comprising an electron donor organic photoconductor and a sensitizing amount of a polycyanoanthracene containing three or more cyano groups.

2. An electrically insulating organic photoconductive composition comprising an electron donor organic photoconductor and a sensitizing amount of 2,6,9,10-tetracyanoanthracene.

3. A photoconductive composition of claim 2 wherein the organic photoconductor is a triarylamine.

4. An electrophotographic element comprising a support bearing a layer of a photoconductive composition of any one of claims 2, or 3.

5. 2,6,9,10-Tetracyanoanthracene.

* * * * *